US006992580B2

(12) United States Patent
Kotzin et al.

(10) Patent No.: US 6,992,580 B2
(45) Date of Patent: Jan. 31, 2006

(54) PORTABLE COMMUNICATION DEVICE AND CORRESPONDING METHOD OF OPERATION

(75) Inventors: Michael D. Kotzin, Buffalo Grove, IL (US); Matthew H. Klapman, Northbrook, IL (US); William P. Alberth, Jr., Crystal Lake, IL (US)

(73) Assignee: Motorola, Inc., Schaumburg, IL (US)

( * ) Notice: Subject to any disclaimer, the term of this patent is extended or adjusted under 35 U.S.C. 154(b) by 16 days.

(21) Appl. No.: 10/206,503

(22) Filed: Jul. 25, 2002

(65) Prior Publication Data

US 2004/0017300 A1   Jan. 29, 2004

(51) Int. Cl.
G08B 1/08    (2006.01)
(52) U.S. Cl. .............................. 340/539.11; 340/573.1
(58) Field of Classification Search ........... 340/539.11, 340/573.1, 539.12, 539.13, 572.1, 825.49, 340/825.69, 573.4; 455/66.1
See application file for complete search history.

(56) References Cited

U.S. PATENT DOCUMENTS

| 5,461,365 | A | * | 10/1995 | Schlager et al. | ......... 340/573.4 |
| 5,544,661 | A | | 8/1996 | Davis et al. | ................. 128/700 |
| 5,559,497 | A | * | 9/1996 | Hong | ....................... 340/573.1 |
| 5,731,757 | A | * | 3/1998 | Layson, Jr. | ............... 340/573.1 |
| 5,923,258 | A | * | 7/1999 | Tseng | .......................... 340/584 |
| 6,076,044 | A | | 6/2000 | Brown | .......................... 702/3 |
| 6,094,141 | A | * | 7/2000 | Tsai | ........................ 340/573.1 |
| 6,100,806 | A | * | 8/2000 | Gaukel | ..................... 340/573.4 |
| 6,225,901 | B1 | * | 5/2001 | Kail, IV | ................ 340/539.11 |
| 6,459,371 | B1 | * | 10/2002 | Pike | ........................ 340/539.1 |
| 6,549,756 | B1 | * | 4/2003 | Engstrom | ................... 455/66.1 |
| 6,593,845 | B1 | * | 7/2003 | Friedman et al. | ......... 340/10.33 |
| 2004/0252867 | A1 | * | 12/2004 | Lan et al. | .................... 382/124 |

* cited by examiner

*Primary Examiner*—Phung T. Nguyen
(74) *Attorney, Agent, or Firm*—Randall S. Vaas; David S. Noskowicz

(57) ABSTRACT

A portable communication device (100) includes at least one sensing circuit (101) and a processor (104), and operates in accordance with a corresponding method of operation. The sensing circuit detects (205) either a characteristic of an external environment containing the portable communication device (e.g., a chemical in the air or acceleration of the device) or a characteristic of the portable communication device user (e.g., heart rate or blood sugar content), and generates a signal (207) representative of a feature of the sensed characteristic. The processor receives the signal and initiates an event based at least on the feature of the sensed characteristic as represented by the signal. Events include, but are not limited to, one or more of the following: alerting the device user, transmitting a signal (e.g., an emergency call) to a remote communication device, re-sensing the characteristic or sensing another characteristic, and modifying a setting or profile of the device.

32 Claims, 4 Drawing Sheets

PORTABLE COMMUNICATION DEVICE AND CORRESPONDING METHOD OF OPERATION

BACKGROUND OF THE INVENTION

The present invention relates generally to portable communication devices and, in particular, to a portable communication device and corresponding method of operation in which portable communication device functionality is expanded to sense or detect various environmental and/or user-related characteristics.

Many environments and conditions within a human body can have a negative, and even fatal, impact on the human body. Humans have five senses in which to try to detect these conditions or environments, but the senses of humans are severely limited. For example, exposure to certain levels of carbon monoxide can cause death; however, carbon monoxide is a gas that cannot be seen, smelled, tasted or felt by human beings. As another example, overexposure to ultraviolet (UV) rays can result in sunburn and, over time, skin cancer or other permanent skin defects, yet humans cannot see, hear, smell, taste or oftentimes even feel the UV ray intensity. By the time a person does feel the UV ray intensity, the person is usually already sunburned. As a further example, an overly rapid heart rate during exercise can result in a heart attack or some other undesired medical condition, yet humans cannot easily detect such a condition with their own senses.

In order to help individuals detect potentially dangerous environments and biological conditions, various personal safety detection devices have been developed for measuring environmental and biological characteristics. Such devices include portable UV meters, such as the "SAFESUN" personal UV meter that is commercially available from Optix Tech Inc. of Washington, D.C., battery-operated carbon monoxide detectors, portable heart rate monitors, and so forth. Although these devices warn their users of potential dangers and, in some cases, may provide additional safety information to their users, they provide no assistance if their users are in trouble and cannot heed the warnings.

Portable communication devices are known to include, inter alia, a receiver, a transmitter, a processor and memory. Such portable communication devices may be wireline or wireless devices, such as two-way radios, pagers, cellular telephones, personal digital assistants (PDAs), laptop computers, and palmtop computers. For wireline devices, the transmitter and receiver are typically embodied in a modem for use with a wireline connection, such as a telephone port connection, a cable access connection, or a connection to one of various other wireline communication services, such as an integrated services digital network (ISDN), or a digital subscriber line (DSL). The modem may be internal to the device, external to the device, or on a personal computer (PC) card (e.g., that complies with the Personal Computer Memory Card International Association (PCMCIA) standard) that may be inserted into the device when necessary. For wireless devices, the transmitter and receiver may be embodied in a wireless radio frequency (RF) modem implemented on a PCMCIA card, or the transmitter and receiver may be separately implemented as part of the wireless device hardware and software architecture.

Portable communication devices are typically carried on or with their users. Thus, the devices generally reside within the same environment as their users. Portable communication devices are typically used for communicating information to a remote communication device and/or for receiving communicated information from a remote communication device. However, portable communication devices may also be used to run various software applications and store information input by their users (e.g., through a keyboard or some other user interface).

Portable communication devices typically include reliability circuitry that senses certain characteristics of the device itself, such as battery level, ambient temperature, time since last user input, and so forth, to enable the device to alert the user of an undesirable device condition (e.g., low battery level) and/or take corrective action (e.g., shut down or begin executing a screen saving software program). However, existing portable communication devices do not include any circuitry that detects potential environmental or biological safety hazards for their users. Consequently, if a user of a portable communication device desires to enhance his or her awareness of certain environmental or biological conditions, the user must use two separate devices: the portable communication device and a personal safety detection device. The use of two devices is not only expensive, but also cumbersome and undesirable for the users.

Therefore, a need exists for a portable communication device and corresponding method of operation that provide a level of personal safety detection, personal function monitoring, and/or environmental information to or for their users.

DETAILED DESCRIPTION OF A PREFERRED EMBODIMENT

Generally, the present invention encompasses a portable communication device and a corresponding method of operation. The portable communication device includes at least one sensing circuit and a processor. The sensing circuit senses or detects characteristics of the users context, which may either be a characteristic of an external environment containing the portable communication device (e.g., a chemical in the air or acceleration of the device) or a characteristic of a user of the portable communication device (e.g., heart rate or blood sugar content), and generates a signal representative of a feature (e.g., intensity, level, modulation, or frequency) of the sensed characteristic. In general, the sensing of a users characteristics is referred to as biometric sensing or biosensing. The processor receives the signal and initiates an event based at least on the feature of the sensed characteristic as represented by the signal. Events include, but are not limited to, one or more of the following: alerting the user of the device, transmitting a signal (e.g., an emergency call) to a remote communication device, re-sensing the characteristic or sensing another characteristic, and modifying a setting or a profile of the portable communication device.

By incorporating sensing circuits in portable communication devices and operating the portable communication devices in this manner, the present invention enables the users of such portable communication devices to essentially extend their own senses to detect characteristics of themselves or their environment, particularly those characteristics that could be potentially harmful to them. For example, by including a carbon monoxide sensor in a cellular telephone, the cellular telephone can alert the phone user in the event that the air in the user's car contains undesirably high levels of carbon monoxide and/or can automatically make an emergency 911 call if the undesirable levels are maintained for a predetermined period of time. Thus, the present invention provides presently unavailable user safety features to portable communication devices and provides for the automatic initiation of an event, such as a telephone call or detection of another characteristic, in the event that an unfavorable level of an initially sensed characteristic is detected and/or maintained for a period of time.

Figure 1:
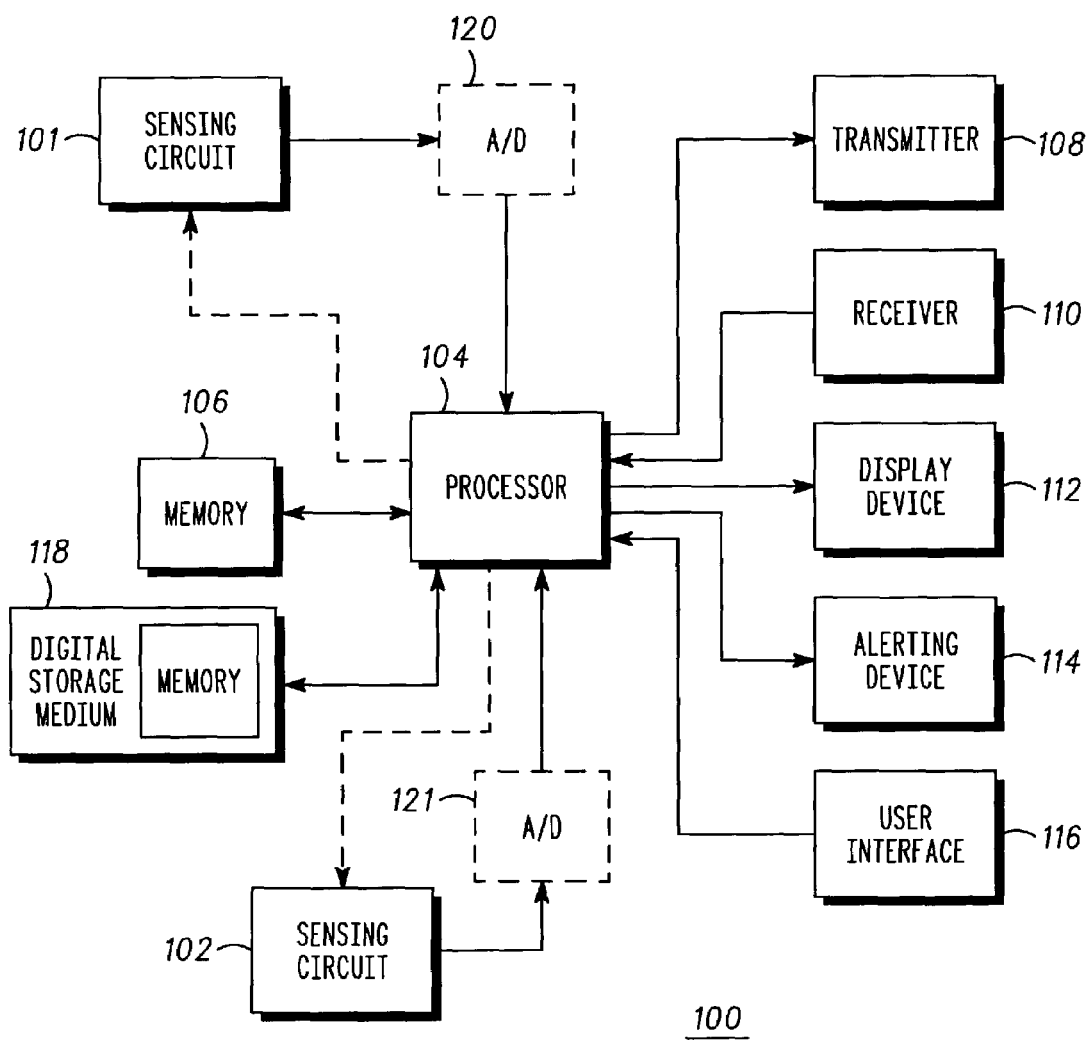
FIG. 1 is a block diagram of a portable communication device in accordance with a preferred embodiment of the present invention.

The present invention can be more fully understood with reference to FIGS. 1–4, in which like reference numerals designate like items. FIG. 1 is a block diagram of a portable communication device 100 in accordance with a preferred embodiment of the present invention. The portable communication device 100 includes one or more sensing circuits 101, 102 (two shown), one or more processors 104 (one shown), memory 106, a transmitter 108, a receiver 110, a display device 112, an alerting device 114, a user interface 116 (e.g., a keypad), and a digital storage medium 118 that includes memory. Memory 116 may reside in the digital storage medium 118 or may be a separate memory component as shown. The communication device 100 may optionally include one or more analog-to-digital converters (A/Ds) 120, 121 (two shown). The A/Ds 120, 121 may be necessary only if the sensing circuits 101, 102 output analog signals that need to be converted to digital bit streams for use by the processor 104. The portable communication device 100 may be any device that is intended to be carried by its user and that functions to facilitate voice, data and/or video communications between a user of the device 100 and another person, machine (e.g., a computer), or network (e.g., a telephone or data network). For example, the portable communication device 100 may be a laptop computer, a palmtop computer, a personal digital assistant (PDA), a wireless communication device (e.g., a two-way radio, a radiotelephone, a pager, or a wireless data terminal), or a cordless telephone or videophone. Thus, the portable communication device 100 may be a wireless or a wireline communication device. In the preferred embodiment, the portable communication device 100 is a portable wireless communication device.

Each sensing circuit 101, 102 (or the sensing circuit when only one such circuit is included) may be any known circuit for sensing or detecting a characteristic of an environment containing the portable communication device 100 or for sensing or detecting a characteristic of a user of the portable communication device 100. For example, each sensing circuit 101, 102 may be:

1) a chemical sensing circuit that senses the presence of gaseous, liquid or solid chemicals in the air, such as a carbon monoxide sensor, a carbon dioxide sensor, a mercury vapor sensor, a breath analyzer circuit (e.g., for detecting the presence of alcohol or other drugs or toxins in the blood), a smoke detector, a pollen sensor, a mold sensor, or a complex protein sensor (e.g., for sensing certain smells);
2) a general environmental sensing circuit, such as a thermometer or temperature sensor, a pressure sensor (e.g., to sense underwater pressure when diving), a humidity sensor, a barometric pressure sensor, or an altitude sensor;
3) a light sensing circuit that detects one or more of amplitude characteristics, color, intensity, wavelength and/or modulation of various forms of light, such as fluorescent light, incandescent light, or sunlight;
4) an electromagnetic radiation sensing circuit that senses a level of electromagnetic radiation within any desired frequency range of the electromagnetic spectrum, such as an ultraviolet (UV) ray sensor, a visible light sensor, an infrared sensor, a radio frequency sensor, an X-ray sensor, or a gamma ray sensor;
5) a magnetic field sensing circuit;
6) an electric field sensing circuit, such as a static charge or microwave sensor;
7) an audio sensing circuit, such as a microphone used to detect background noise;
8) a biological or biometric sensing circuit that detects a characteristic of the device user, such as pulse, heart rate, blood pressure, respiration peak flow, blood oxygen level, EEG, glucose level, heart rhythm (e.g., an electrocardiogram (EKG), or skin conductivity;
9) a radioactivity sensing circuit, such as a Geiger counter, that detects alpha rays or beta rays;
10) a distance sensing circuit to detect the range of the portable communication device from an object; or
11) an acceleration/deceleration sensing circuit to detect whether the portable communication device is in motion.

All of the above sensing circuits are known and are employed in various commercially available, medical, personal safety and other non-communicating devices. Slight modifications to such commercially available sensing circuits may be necessary in accordance with the present invention to enable the particular sensing circuit to sense features other than intensity or level, such as exposure, modulation and/or wavelength. For example, if the output of a sensing circuit 101, 102 is instantaneous UV intensity, integration of the sensing circuit output signal over time in accordance with known techniques may be performed to estimate the device user's actual UV exposure. Additional processing necessary to determine features, such as exposure, modulation and/or wavelength, may be provided using known analog or digital signal processing techniques within the portable communication device 100 (e.g., within the processor 104). Other functions available within the portable communication device 100 may also be used advantageously in accordance with the present invention. For example, a real-time clock of the device 100 may be used to aid in determining variable thresholds or conditions upon which to create user alarms.

Examples of known sensing circuits include silicon strain pressure sensors and accelerometers which are commercially available from Motorola, Inc. of Schaumburg, Ill., UV sensors as employed in the "SAFESUN" personal UV meters that are commercially available from Optix Tech Inc. of Washington, D.C., and heart rate sensors as employed in personal heart rate monitors that are commercially available from various manufacturers, such as Polar Electro Inc. of Woodbury, N.Y. Although the sensing circuits themselves are known, their uses have been limited to devices that do not provide any communication functionality. By contrast, the present invention discloses and claims a portable communication device in which one or more sensing circuits are employed to enhance the features, particularly the safety features, of such communication devices.

The processor 104 preferably includes one or more microprocessors, microcontrollers, DSPs, or state machines, logic circuitry, or any other device or devices that process information based on operational or programming instructions. Such operational or programming instructions are preferably stored in a memory of digital storage medium 118, which medium 118 may be an integrated circuit (IC) memory chip containing any form of random access memory (RAM) or read only memory (ROM), a floppy disk, a compact disk read only memory (CD-ROM), a hard disk drive, a digital versatile disk (DVD), a flash memory card or any other medium for storing digital information. However, one of ordinary skill in the art will recognize that when the processor 104 has one or more of its functions performed by a state machine or logic circuitry, the memory containing the corresponding operational instructions may be embedded within the state machine or logic circuitry. The operations performed by the processor 104 and the rest of the portable communication device 100 are described in detail below.

Memory 106 may be any form of RAM or ROM and is used for, inter alia, storing one or more settings of the communication device 100, including thresholds related to sensed characteristics. For example, memory 106 may be used to store a profile of the portable communication device 100 and/or user preferences. As noted above, memory 106 may reside in digital storage medium 118.

The transmitter 108 and the receiver 110 are well-known components of two-way communication devices. The transmitter 108 and the receiver 110 enable the portable communication device to communicate signals to and acquire communicated signals from other, remotely located communication devices. The implementation of the transmitter 108 and the receiver 110 depends on the implementation of the portable communication device 100. For example, for a wireline portable communication device 100, the transmitter 108 and the receiver 110 are preferably embodied in a modem for use with a wireline connection, such as a telephone port connection, a cable access connection, or a connection to one of various other wireline communication services, such as an integrated services digital network (ISDN), or a digital subscriber line (DSL). The modem may be internal to the device 100, external to the device 100, or on a personal computer (PC) card (e.g., that complies with the Personal Computer Memory Card International Association (PCMCIA) standard) that may be inserted into the device 100 when necessary. Alternatively, for a wireless portable communication device 100, the transmitter 108 and the receiver 110 are preferably separately implemented as part of the wireless device hardware and software architecture in accordance with known techniques, or may be embodied in a wireless RF modem implemented on a PCMCIA card. One of ordinary skill in the art will recognize that all or most of the functions of the transmitter 108 and/or the receiver 110 may be implemented in a processor, such as processor 104. However, the processor 104, the receiver 110 and the transmitter 108 have been artificially partitioned herein to facilitate a better understanding of the present invention.

The display device 112 may be any conventional cathode ray tube (CRT) display, liquid crystal display (LCD), or other display. The alerting device 114 may be any conventional audible or silent alerting mechanism, such as a tone generator (to produce a beeping alert tone) or a vibration system (to produce a vibratory alert). The user interface 116 may be any conventional user interface, such as a keyboard, a keypad, a touchscreen, a mouse or rollerball, a touchpad, or any combination of the foregoing. In addition, when the portable communication device 100 includes circuitry for sensing a characteristic of the user of the device 100, the user interface 116 may include other components, such as probes, cables and/or other known circuitry for coupling the sensing circuit 101, 102 to the skin of the user.

Operation of the portable communication device 100 occurs substantially as follows in accordance with the present invention. Each sensing circuit 101, 102 senses or detects a particular characteristic of the environment containing the portable communication device 100 or a particular characteristic of the user of the portable communication device 100. For example, all the sensing circuits 101, 102 may sense different characteristics of the environment or of the user, or some of the sensing circuits 101 may sense characteristics of the environment, while other sensing circuits 102 sense characteristics of the user. When the portable communication device 100 includes only one sensing circuit 101, the sensing circuit 101 senses either a characteristic of the environment containing the portable communication device 100 or a characteristic of the user of the device 100.

The sensing circuits 101, 102 may operate independently (e.g., continuously) or under the control of the processor 104 (i.e., sense or detect only in response to a control signal (e.g., control voltage) received from the processor 104). In one embodiment in which the sensing circuits 101, 102 are under the control of the processor 104, the processor 104 may instruct the sensing circuits 101, 102 to sense their respective characteristics responsive to receiving a sensing command from a remote communication device, such as a system controller, a public safety answering point (PSAP), any portable communication device, or any fixed communication device. For example, a colleague or co-worker may initiate sensing by another colleague's or co-worker's portable communication device by sending a sensing command to the device. In such a case, the receiver 110 of the sensing device 100 receives the sensing command, demodulates and decodes it in accordance with the communication protocol for the communication link between the devices, and provides a digital representation of the sensing command to the processor 104. Alternatively, the received sensing command may be provided directly to the processor 104 for demodulation and decoding when the receiver function is embodied in the processor 104 as noted above. The processor 104, upon receiving the digital representation or decoding the sensing command directly, instructs the sensing circuit or circuits 101, 102 to sense their respective characteristic or characteristics. The sensing command may include the identity of a particular characteristic to be sensed or the timing of the sensing (e.g., immediately or at some later time). Therefore, the device initiates a first sensor measurement of a sensed characteristic in response to the command by the remote device. In addition, an algorithm may be established in the device in response to the command or the sensor measurement meeting a first criteria. This algorithm may alter the predetermined measurement parameters of any of the sensing circuits in the device. It may alter the parameters for one or all or a subset of all the sensing circuits. An example of the parameters that may be altered by the algorithm would be the threshold level of the sensed characteristic, the measurement frequency, the threshold level that triggers a measurement, the sequence of measurements taken, the response to a given measurement (i.e. a phone call is made, the user is alerted). The algorithm may also initiate a second sensor measurement of a sensed characteristic.

The sensing circuits 101, 102 generate output signals representative of levels (e.g., amplitudes or intensities) or other features (e.g., modulation or frequency) of the sensed characteristics. The output signals are preferably digital signals that are provided directly to the processor 104. Alternatively, the sensing circuit output signals may be analog signals, in which case, the output signals are preferably provided to A/Ds 120, 121 for conversion into digital signals to be provided to the processor 104.

Upon receiving the digital signals from the sensing circuits 101, 102 or the A/Ds 120, 121 (or the sensing circuit 101 or the AID 120 when the portable communication device 100 includes only one such circuit or AID), the processor 104, in accordance with operating instructions stored in the memory of the digital storage medium 118, evaluates the signals to determine the features of the sensed characteristics present in the signals. For example, the processor 104 determines whether the signals represent levels of sensed characteristics or represent other features of the sensed characteristics, such as wavelength (e.g., where a sensed characteristic is light), frequency or rate (e.g., where a sensed characteristic is electromagnetic radiation or heart rate), or modulation (e.g., where a sensed characteristic is light or electromagnetic radiation). The processor 104 may make such a determination based on the identities of the sensing circuits 101, 102 that generated the signals (e.g., a temperature or carbon monoxide sensing circuit generates signals representative of the levels of the sensed characteristics), other parameters of the sensing circuits 101, 102, regular variations in an attribute (e.g., frequency or amplitude) of the received signal, and/or the time of day.

In the event that the digital signals provided to the processor 104 represent levels of the sensed characteristics, the processor 104 preferably compares the levels to respective thresholds or threshold ranges stored in memory 106. Depending upon the outcome of the comparisons in view of programmed operational rules stored in the digital storage medium 118, the processor 104 may automatically initiate one or more events. For example, if the processor 104 determines that the level of one of the sensed characteristics (or the level of the sensed characteristic when only one sensing circuit 101 is employed) is unfavorable with respect to the characteristic's corresponding threshold, the processor 104 preferably automatically initiates an event. In the preferred embodiment, the processor 104 considers a sensed characteristic's level to be unfavorable if the level exceeds a maximum threshold, is less than a minimum threshold, or is outside a desirable range of values stored in the memory 106. Exemplary events include activating the alerting device 114 to alert the user of the undesirable condition, instructing the transmitter 108 to transmit a signal, such as an emergency call, to a remote communication device, instructing another sensing circuit 102 to sense its particular characteristic, instructing the same sensing circuit 101 to re-sense its characteristic, modifying a prestored device setting, and/or modifying multiple prestored device settings (e.g., modifying a device profile).

The communication function of the portable communication device 100 may be used to enhance the versatility and flexibility of the threshold and threshold ranges related to the sensed characteristics. For example, the thresholds and/or ranges may be downloaded from or altered by a remote device via a control protocol supported by the communication link between the portable communication device 100 and the remote device.

Limitations on what functions, including events, may be performed by the portable communication device 100 may be stored in memory 106 as part of the device settings. For example, the device settings may restrict the type of call the portable communication device 100 may make under certain circumstances. For instance, the device settings may restrict calls initiated by the device 100 to be directed only to prestored (e.g., speed dial) or emergency telephone numbers when an acceleration sensing circuit detects that the device 100 is in motion. As indicated above, certain events initiated by the device 100 in response to signals received from one or more of the sensing circuits 101, 102 may result in modifications to one or more device settings, including the threshold or thresholds against which the sensed characteristic features represented by the signals are compared. For example, the UV exposure threshold may be modified based on the time of day and/or the temperature of the device 100. For instance, the threshold may be increased between the hours of 4:00 PM and 10:00 A M to reduce the likelihood of false alarms during the time of the day when sun intensity is at its minimum. In addition, the sensed temperature of the device 100 may be used to adjust the UV exposure threshold since temperature can be used to determine whether the user may be inside a building, but merely near a window.

In one embodiment, the alerting device may not be a separate device, but rather may form part of the display device 112. In such an embodiment, when the event to be initiated is activating the alerting device, the processor 104 modifies a display of the display device 112 to alert the user of the undesirable condition. For example, the processor 104 may blink the display, blank the display or change the display color to alert the device user of the condition.

The evaluation rules stored in the digital storage medium 118 preferably define how the processor 104 evaluates the signals received from the sensing circuits 101, 102. The rules may provide for the processor 104 to evaluate each received signal with respect to a corresponding threshold as discussed above. Alternatively, the rules may provide for the processor 104 to integrate levels of a sensed characteristic received by the processor 104 over a period of time to determine an exposure level and then compare the exposure level to a corresponding exposure threshold, instead of performing multiple characteristic level comparisons in real time. For example, if the sensed characteristic is UV ray intensity, such intensity may be harmful only when a person has been subjected to it for a period of time. In this case, an exposure evaluation is more applicable than an instantaneous intensity. The rules programmed for a particular portable communication device 100 identify which sensed characteristic, if any, should be evaluated on a long-term (e.g., minutes or hours) exposure basis as opposed to an instantaneous or other shorter period basis. Still further, the rules may provide for the processor 104 to simultaneously evaluate multiple sensed characteristics (e.g., temperature and light intensity) to determine whether an event should be initiated. For example, as noted above, temperature, time of day, and UV exposure may be simultaneously evaluated to determine whether the user should be alerted of a potentially dangerous exposure to UV radiation. One of ordinary skill in the art will recognize and appreciate that various other rules may be promulgated for initiating one or more events responsive to evaluating levels or other features of one or more sensed characteristics. Such other rules are intended to fall within the spirit and scope of the present invention as recited in the appended claims.

In addition to sensing characteristics related to either the environment containing the communication device 100 or the user of the communication device 100, the communication device 100 performs other conventional communication functions, such as transmitting voice, data and/or video communications to remote communication devices via the transmitter 108 and/or receiving voice, data and/or video communications from remote communication devices via the receiver 110. The display device 112, the alerting device 114 (e.g., ringer or vibration mechanism), and the user interface 116 are all also preferably used in accordance with known techniques to perform conventional functions related to communications. For example, the display device 112 is preferably used to display digits of a dialed telephone number, menu options, a received short text message, or various other text or graphics items typically displayed during operation of a portable communication device 100. Similarly, the alerting device 114 indicates receipt of a call or message from a remote communication device, and the user interface 116 is used by the device user to select menu options, dial telephone numbers, and perform various other conventional user operations. Further, the processor 104 preferably operates in accordance with other stored operating instructions to carry out the various communication functions of the communication device 100.

As described above, the present invention provides a portable communication device that, in addition to performing conventional communication functions, senses one or more characteristics of an environment containing the communication device and/or one or more characteristics of a user of the communication device. Instead of requiring two separate devices for communication and sensing as in the prior art, the present invention incorporates both functions into a portable communication device. Further, the present invention provides for automatic event initiation by the communication device in response to certain features of the sensed characteristics. Thus, the present invention inter-relates communication and sensing functions to provide personal safety features to portable communication devices. Such personal safety features are not present in prior art portable communication devices. Still further, the present invention provides for remote control of the portable communication device's sensing operations to enable a remote communication device or a remote communication device user to initiate sensing in the portable communication device. Such remotely-controlled sensing enables a remote individual to initiate device sensing operations in the event that the device is not initiating such operations automatically or in the event that the device user is presently not capable of instructing the device to initiate such sensing operations.

Figure 2:
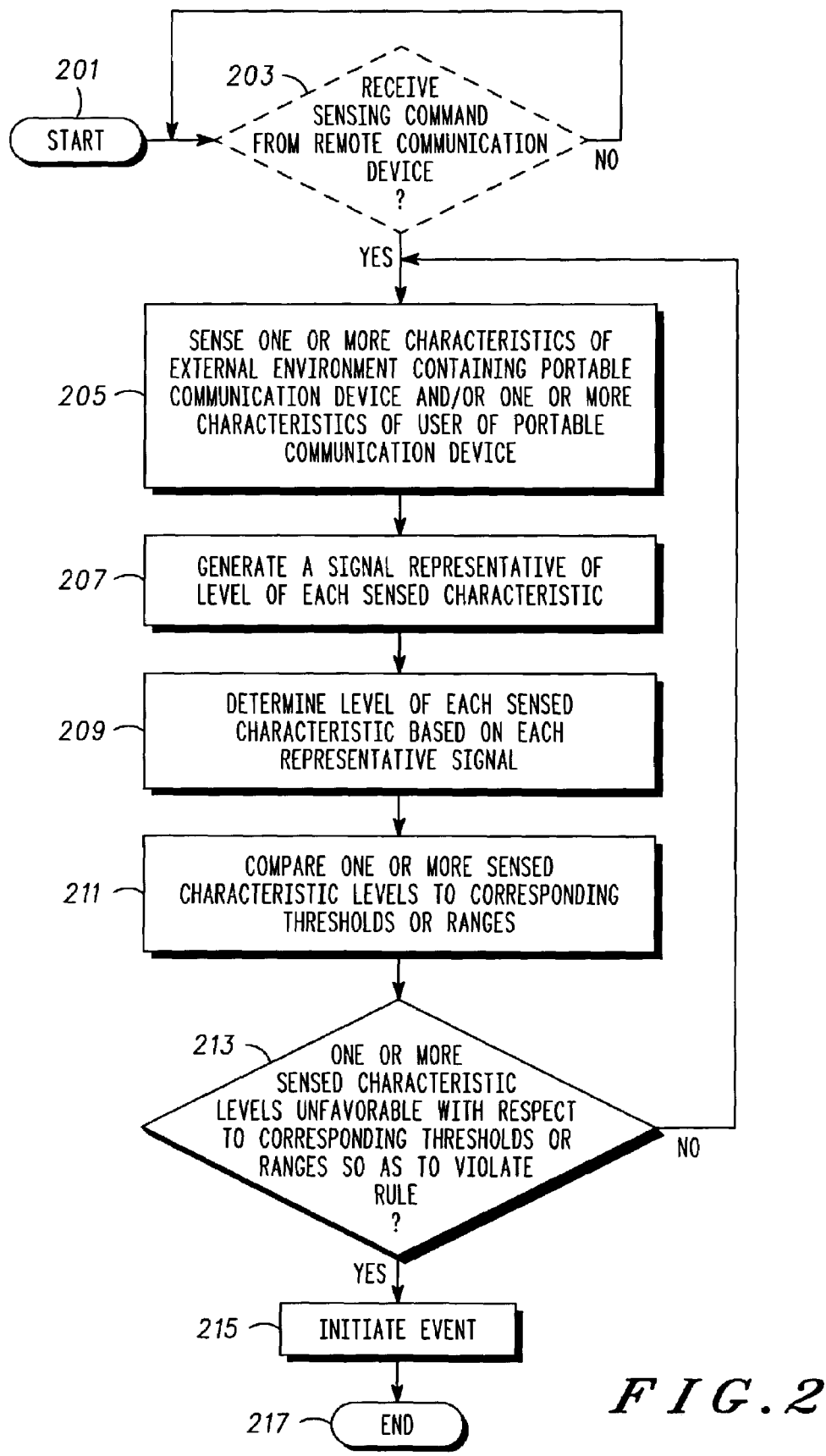
FIG. 2 is a logic flow diagram of steps executed by a portable communication device during operation of the portable communication device in accordance with one embodiment of the present invention.

FIG. 2 is a logic flow diagram 200 of steps executed by a portable communication device in accordance with one embodiment of the present invention. The logic flow begins (201) when the portable communication device optionally receives (203) a sensing command from a remote communication device. As discussed above, the characteristic sensing or detection performed by the portable communication device may be carried out unilaterally or in response to an instruction received from a remote device, such as a central computer at a police or fire rescue station. When characteristic sensing is performed responsive to receipt of a sensing command, the sensing command is received in accordance with the receive protocol of the communication system in which the portable communication device is operating. For example, if the portable communication device is a cellular telephone operating in accordance with the Global System for Mobile (GSM) Communications standard, then the sensing command may be received over an assigned traffic channel or over a control channel (e.g., where the sensing command is issued by the system controller) in accordance with the GSM standard. Alternatively, if the portable communication device is a laptop computer connected to a telephone data port, the sensing command may be received in accordance with telephony data standards.

In the event no sensing command is received and the portable communication device is programmed to perform characteristic sensing responsive to receipt of such a command, the portable communication device continues monitoring for receipt of a sensing command. In the event that a sensing command is-received or the portable communication device unilaterally (e.g., continuously, periodically or even randomly) performs the sensing operation, the portable communication device senses (205) or detects one or more characteristics of an external environment containing the portable communication device and/or one or more characteristics of a user of the portable communication device. That is, the portable communication device utilizes one or more of its pre-installed sensing circuits to sense or detect a characteristic of the environment containing the portable communication device (and likely also containing the user of the communication device), such as a level of carbon monoxide, a level of ambient light to facilitate a determination as to whether the communication device is inside or outside a building, a pressure level, an acceleration level, or any other environmental characteristic, and/or a characteristic of the user of the portable communication device, such as a heart rate, a glucose level, or any other biological characteristic. As discussed above, the portable communication device may include one or more sensing circuits to detect such characteristics. For example, the portable communication device may include one or more sensing circuits to sense only environment-related characteristics, may include one or more sensing circuits to sense only user-related characteristics, or may include multiple sensing circuits to sense one or more environment-related characteristics and one or more user-related characteristics.

After the particular characteristic or characteristics have been sensed, the portable communication device generates (207) a signal (e.g., a bit stream) representative of each sensed characteristic. Consequently, when only one environment-related or user-related characteristic is sensed, only one signal is generated. However, multiple signals may be generated by sensing a single characteristic multiple times over a selected time period as discussed in more detail below with respect to FIG. 3. When multiple characteristics are sensed, multiple signals are generated, each representing a level or some other feature of a particular sensed characteristic. The signals are preferably digital signals generated directly by the circuits performing the sensing operations in accordance with known techniques. Alternatively, the signals may be analog signals (analog voltages or currents) generated directly by the sensing circuits or digitally converted representations of such analog signals generated by one or more A/D converters.

Once a signal representative of each sensed characteristic is generated, the portable communication device determines (209) a level of each sensed characteristic based on the corresponding representative signal. That is, the portable communication device, preferably through operations carried out by its processor, determines an amplitude of each sensed characteristic represented by a signal. For an analog signal, such a determination may be made by measuring the amplitude of the analog signal (e.g., voltage or current). For a digital signal, such a determination may be made by evaluating a value of a predetermined number of bits used to represent the level of the sensed characteristic (e.g., two bytes or sixteen bits may represent an amplitude of the sensed characteristic). In the event that the portable communication device senses several characteristics, the portable communication device may determine levels for only a subset of the characteristics to reduce the amount of processing time and resources necessary to make such determinations. The subset of characteristics to be evaluated may be limited by various programmable rules, such as whether the portable communication device is inside or outside, time of day, if the device is connected to a network such as a telematics automobile network or an in-building Bluetooth network, or user indication. One method for determining whether the portable communication is inside or outside a building is described below with respect to FIG. 4. One of ordinary skill in the art will appreciate that the determination of whether or not the portable communication device is inside or outside an enclosure, such as a building or automobile, is also a manner of sensing an environmental characteristic of the portable communication device (i.e., whether the device is in an inside environment or in an outside environment).

After the amplitude or level of each sensed characteristic or each of a subset of characteristics is determined, the portable communication device compares (211) one or more of the sensed characteristic levels to corresponding thresholds or threshold ranges stored in a memory of the communication device. For example, if the sensed characteristics are acceleration (or deceleration) and ambient noise, a level of each characteristic may be sensed and compared to a respective threshold or threshold range to determine whether the portable communication device was in a car accident. Responsive to the comparison or comparisons, the portable communication device determines (213) whether the levels of the sensed characteristics are unfavorable with respect to their corresponding thresholds or threshold ranges so as to violate a programmed rule. That is, the portable communication device, preferably through operation of its processor, determines whether the levels of sensed characteristics having low acceptable safety levels, such as radioactivity or carbon monoxide, are less than or equal to their corresponding maximum safety thresholds, whether the levels of sensed characteristics having high acceptable safety levels, such as oxygen, are greater than or equal to their corresponding minimum safety thresholds, and whether the levels of sensed characteristics having a range of acceptable safety levels, such as heart rate or glucose level, fall within their corresponding acceptable safety ranges.

For example, a portable communication device may include several sensors or sensing circuits, some of which are evaluated by the device's processor independently, some of which are evaluated only in combination with one or more other sensing circuits, and some of which are evaluated both independently and in combination with other sensing circuits. For instance, the portable communication device may include a temperature sensing circuit, a light sensing circuit, a carbon monoxide sensing circuit, and a heart rate sensing circuit. The temperature and light sensing circuits may be evaluated in combination to enable the portable communication device to determine whether it is inside or outside. In addition, the carbon monoxide sensing circuit and the heart rate sensing circuit may be evaluated together to indicate whether the device user may be in danger due to the presence of carbon monoxide in the air. Further, all of the sensing circuits may be evaluated independently to determine if any danger exists based solely on their individual levels with respect to their corresponding thresholds.

In the event that one or more of the levels of the sensed characteristics are determined to be unfavorable with respect to their corresponding thresholds or threshold ranges so as to violate a programmed rule, the portable communication device initiates (215) an event, and the logic flow ends (217). The processor of the portable communication device is preferably programmed with various rules for use in analyzing the signals received from the sensing circuit or circuits. Violation of each rule results in initiation of a particular event. As noted above, the events include, but are not limited to, alerting a user of the communication device either by activating an alerting device, such as a vibration mechanism or tone generation circuitry, or by modifying a display of a display device, automatically transmitting a signal, such as an emergency signal, to another communication device (e.g., automatically placing a 911 call), automatically re-sensing the characteristic or characteristics whose level or levels resulted in initiation of the event, automatically sensing a different characteristic (e.g., a characteristic that may further indicate whether a dangerous condition is present), modifying one or more prestored settings (e.g., a profile) of the communication device (which may include modifying the threshold of the sensed characteristic or characteristics whose level or levels resulted in initiation of the event), or any combination of the foregoing events.

For example, the portable communication device's processor may be programmed to include a rule in which an alerting device is activated and periodic re-sensing of a sensed characteristic occurs when the level of the sensed characteristic enters an unfavorable range. If subsequent sensing of the characteristic does not result in a reduction of the characteristic's level or the communication device user has not indicated (e.g., through use of the device's user interface) that subsequent sensing need not be performed (e.g., indicating that the communication device user has taken heed of the alert), the rule may provide for a predetermined signal (e.g., an emergency signal) to be automatically transmitted to a remote communication device to alert the user of the remote device that a potentially dangerous condition may be affecting the portable communication device user. As was described above with respect to receipt of a sensing command from a remote device, transmission of a signal to a remote device complies with the transmission protocol of the link between the portable communication device and the remote device.

Alternatively, the rule may provide for a different characteristic to be sensed if the level of the originally sensed characteristic does not improve over time. Still further, the rule may provide for selection of the event based further on the time of day and/or an indication or input by the portable communication device user. For example, an alert may be provided first during work hours (i.e., when a user of the device is likely located sufficiently close to the device to detect the alert) followed by automatic transmission of an emergency call if no improvement is detected in the level of the sensed characteristic; whereas, an automatic transmission to a remote device (e.g., a security monitoring company or the police) may be the only event initiated in response to detection of an unfavorable level of the sensed characteristic during off hours. One of ordinary skill in the art will appreciate that various other rules may be employed depending on the particular sensing circuits embodied in the portable communication device.

In the preferred embodiment, steps 209, 211, 213, and 215 are carried out by a processor, such as a microprocessor or a digital signal processor (DSP), executing a software algorithm (algorithm) stored in memory of a digital storage medium, such as an integrated circuit memory chip (e.g., ROM or RAM), a floppy disk, a CD-ROM, a DVD, a flash memory card, or hard disk. Alternatively, such steps may be implemented in firmware or hardware, such as in an application specific integrated circuit (ASIC).

Figure 3:
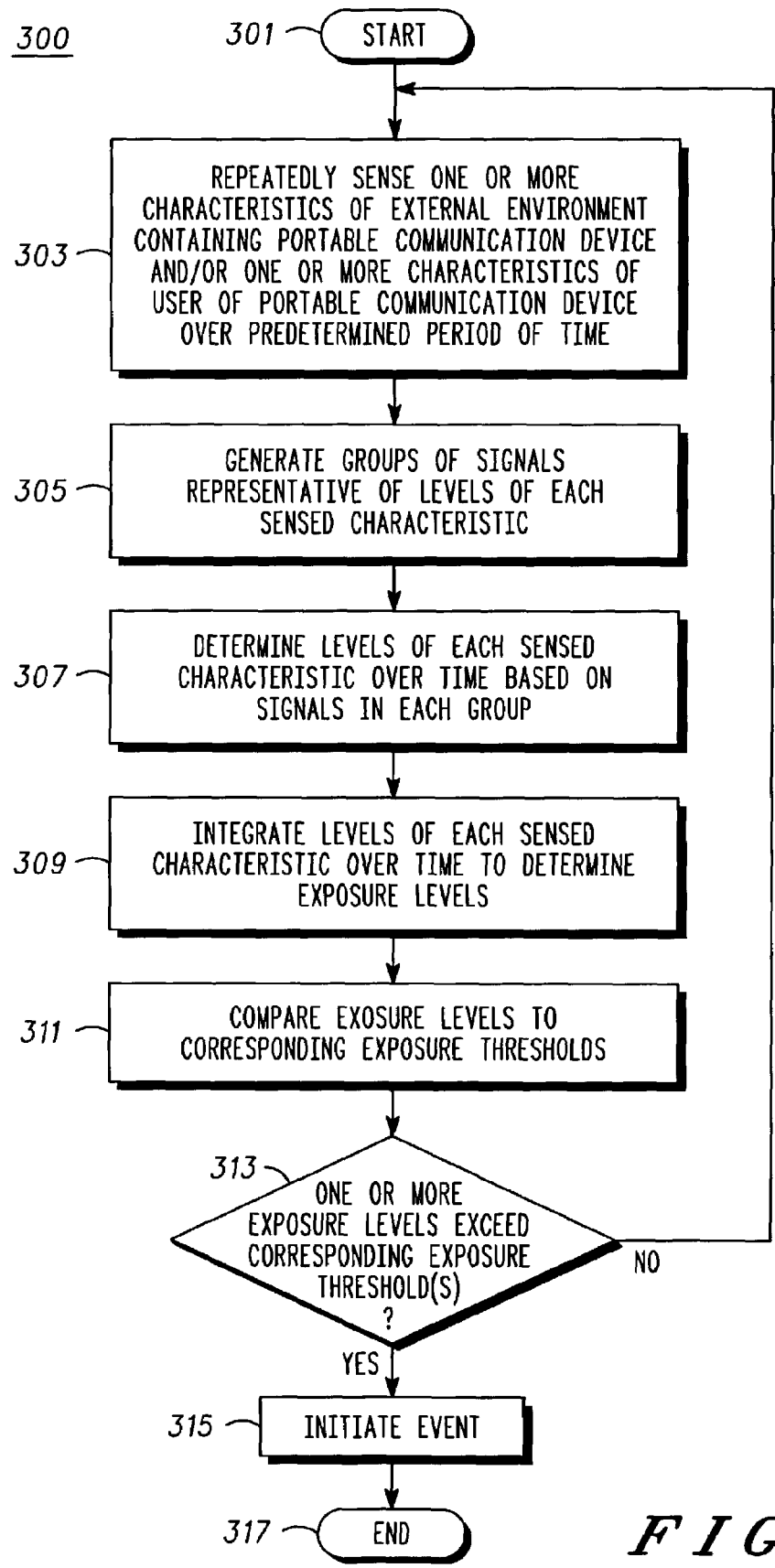
FIG. 3 is a logic flow diagram of steps executed by a portable communication device during operation of the portable communication device in accordance with another embodiment of the present invention.

FIG. 3 is a logic flow diagram 300 of steps executed by a portable communication device in accordance with another embodiment of the present invention. The logic flow diagram 300 of FIG. 3 is similar to the logic flow diagram 200 of FIG. 2, except that each sensed characteristic or certain selected sensed characteristics are repeatedly sensed over time to enable the portable device's processor to integrate the levels of the sensed characteristics over time to determine the device's (and likely the device user's) exposure to the particular characteristic. The logic flow begins (301) when the portable communication device repeatedly (e.g., periodically) senses (303) one or more characteristics of an external environment containing the portable communication device and/or one or more characteristics of a user of the portable communication device. That is, the portable communication device utilizes one or more of its pre-installed sensing circuits to sense or detect a characteristic of the environment containing the portable communication device (and likely also containing the user of the communication device) and/or a characteristic (e.g., a biological characteristic) of the user of the portable communication device over a period of time (e.g., several seconds or several minutes). Responsive to the repeated sensing, the portable communication device generates (305) groups of signals representative of the levels of each characteristic or selected characteristics that were sensed over the time period. As discussed above with respect to FIGS. 1 and 2, each group of signals are preferably generated directly by the respective sensing circuit or by an A/D converter coupled to an output of the sensing circuit.

After or as a group of signals representative of levels of a sensed characteristic are generated over the time period, the portable communication device, preferably through operations carried out by its processor, determines (307) the levels of the sensed characteristic over time based on the signals in the group. Such a determination may be performed for each sensed characteristic or for only one or more selected sensed characteristics. As discussed above with respect to FIG. 2, the portable communication device processor preferably determines time-varying amplitudes or levels of the sensed characteristic represented by the groups of signals. After determining the time-varying levels of the sensed characteristic, the portable communication device integrates (309) the levels of the sensed characteristic over the time period to determine an exposure level with respect to the sensed characteristic. Such integration may be performed for each sensed characteristic or for only one or more selected sensed characteristics.

Once one or more exposure levels are determined, the portable communication device compares (311) the exposure level or levels to corresponding exposure thresholds stored in a memory of the communication device. Sensed characteristics for which integration may be beneficially employed include many, if not all, of the environment-related and user-related characteristics identified above with respect to FIG. 1. The portable communication device then determines (313), based on the comparison(s), whether one or more of the exposure levels exceeds their corresponding exposure thresholds. For example, the portable communication device, preferably through operation of its processor, attempts to determine whether the portable communication device and/or its user has received an undesirable amount of exposure to potentially harmful environmental or biological conditions. When the portable communication device determines that a single exposure threshold has been exceeded or that multiple related exposure thresholds (i.e., exposure thresholds for related characteristics) have been exceeded, the portable communication device initiates (315) an event and the logic flow ends (317); otherwise, the device continues sensing (303) one or more characteristics. The initiated event may be any one or more of the exemplary events listed above with respect to FIGS. 1 and 2, or any other event.

In the preferred embodiment, steps 307, 309, 311, 313 and 315 are carried out by a processor, such as a microprocessor or a DSP, executing a software algorithm stored in memory of a digital storage medium, such as an integrated circuit memory chip (e.g., ROM or RAM), a floppy disk, a CD-ROM, a DVD, a flash memory card, or hard disk. Alternatively, such steps may be implemented in firmware or hardware, such as in an ASIC.

Figure 4:
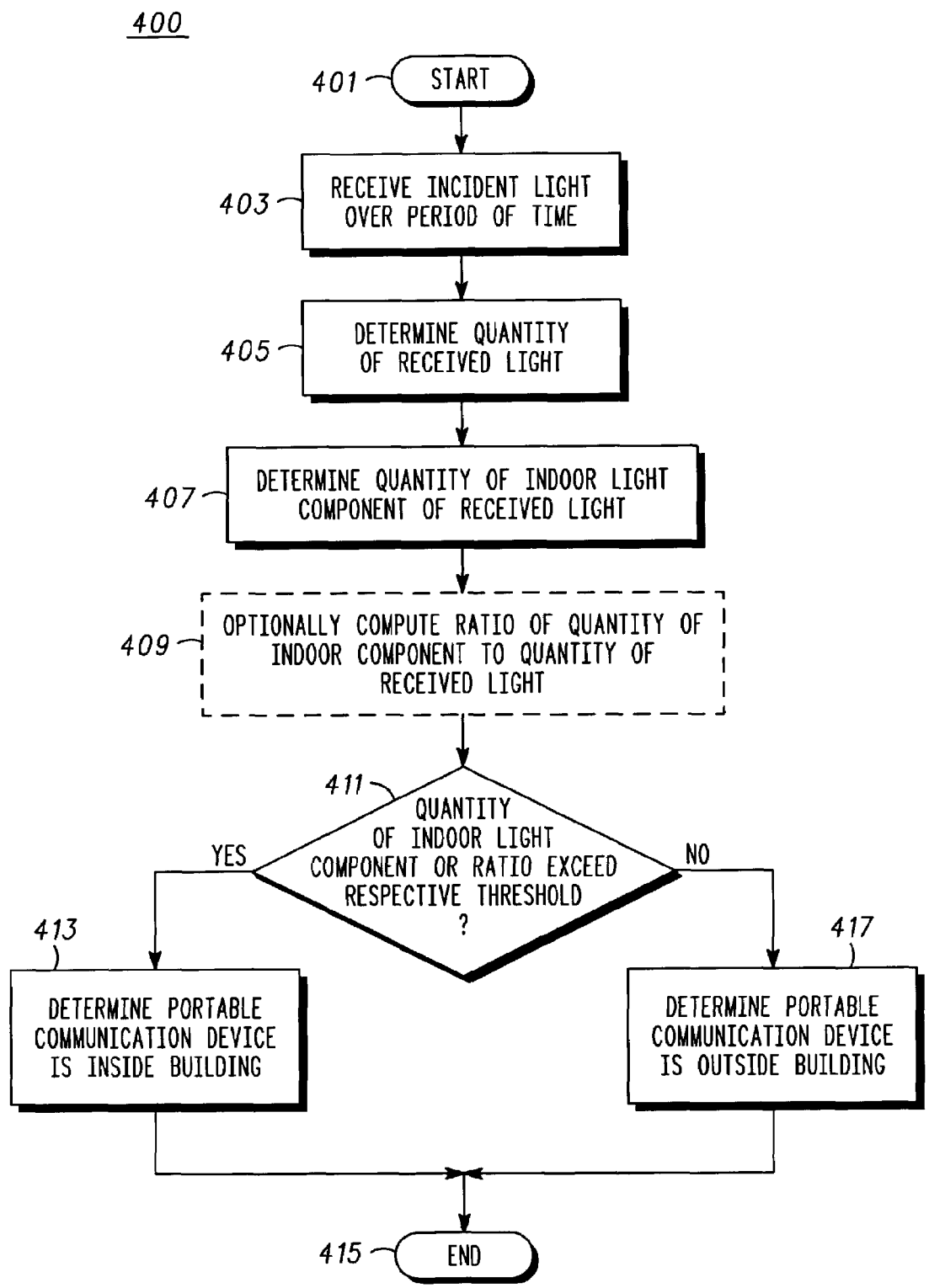
FIG. 4 is a logic flow diagram of steps executed by a portable communication device to determine whether the portable communication device is inside or outside a building in accordance with a particular embodiment of the present invention.

FIG. 4 is a logic flow diagram 400 of steps executed by a portable communication device to determine whether the portable communication device is inside or outside a building in accordance with a particular embodiment of the present invention. The logic flow begins (401) when the portable communication device receives (403) incident light over a period of time. A light sensing circuit, such as a silicon phototransistor or a CMOS sensor together with appropriate signal buffering, filtering and amplifying circuitry, may be used to receive the incident light in accordance with known techniques. After the light is received, the portable communication device determines (405) a quantity of received light (e.g., a maximum or average amplitude of the received light) in accordance with known techniques. In addition, the portable communication device determines (407) a quantity of an indoor light component of the received light. In one embodiment, such a determination is made by filtering out the fifty or sixty Hertz (Hz) component of the received light and measuring the filtered component's amplitude (either maximum or average to coincide with the measured quantity of received light) using an amplitude detector (and an integrator when an average value is desired). As is known, ambient light generated from electric light bulbs typically includes a fifty or sixty Hertz component depending on the electric power standards of the country in which the building is located.

The portable communication device, preferably through operation of its processor, then optionally computes (409) a ratio of the quantity of the indoor light component to the quantity of the overall received light and compares (411) either the quantity of the indoor light component or the ratio (when computed) to a corresponding threshold stored in memory. When the compared value (quantity of indoor light or ratio) exceeds its respective threshold, the portable communication device determines (413) that the portable communication device is more than likely inside a building and the logic flow ends (415). Alternatively, when the compared value is less than or equal to its respective threshold, the portable communication device determines (417) that the portable communication device is more than likely outside a building. To increase the accuracy of the inside/outside determination, the portable communication device may also sense the temperature and use the temperature as an additional factor in deciding whether the portable communication device is inside or outside in the event that the level of the indoor light component or the ratio exceeds the threshold, but is within a range of levels encountered when a person stands outside a window of an illuminated building.

The present invention encompasses a portable communication device and corresponding method of operation. With this invention, various environmental and/or biological sensing operations are added to the features of a portable communication device. Features of sensed characteristics, such as intensity, wavelength, modulation, and exposure level, are evaluated by the portable communication device against prestored thresholds or other parameters. In accordance with certain programmed rules, the portable communication device automatically initiates an event based on the evaluated feature or features of the sensed characteristic. For example, the portable communication device may automatically make an emergency call upon detecting an abnormally high level or intensity of a sensed characteristic. In another example the portable communication device would interface to an automobile over a network such as a telematics network. If the driver suffered a heart attack the portable communication device would sense the health problem automatically make an emergency call, and order the car to disable the accelerator and to apply the brakes. Thus, the present invention integrates characteristic sensing and communications to improve personal and public safety of portable communication device users. In addition, the present invention facilitates remote activation of the portable communication device's sensing operations, such as in the event that the device is not programmed to automatically engage in such operations and/or the device user is incapacitated. Further, the present invention provides for sensing multiple characteristics simultaneously or in a particular order (e.g., sensing one characteristic if a level of another characteristic is unfavorable) to obtain a potentially better overall picture of the device's (and likely the device user's) environment or the device user's physical condition. Further still, the invention allows the device to request modifications to the environment. For example, a user may have an intolerance to cold. The device upon sensing a temperature could request over Bluetooth that the building reduce the air conditioning in the occupied room.

In the foregoing specification, the present invention has been described with reference to specific embodiments. However, one of ordinary skill in the art will appreciate that various modifications and changes may be made without departing from the spirit and scope of the present invention as set forth in the appended claims. For example, the sensing circuits need not be used solely to monitor for dangerous conditions. Rather, the sensing circuits may also or alternatively be used for informational purposes. For instance, the portable communication device may include a circuit that senses certain complex proteins (e.g., smells) in the air to inform the user as to the source of an aroma. Such a complex protein sensing circuit may be found in the "CYRANOSE" and "NOSE-CHIP" artificial nose products that are commercially available from Cyrano Sciences Inc. of Pasadena, Calif. Alternatively, the portable communication device may be programmed to perform sensing operations only upon request either from the communication device user or from a remote communication device. Accordingly, the specification and drawings are to be regarded in an illustrative rather than a restrictive sense, and all such modifications are intended to be included within the scope of the present invention.

Benefits, other advantages, and solutions to problems have been described above with regard to specific embodiments of the present invention. However, the benefits, advantages, solutions to problems, and any element(s) that may cause or result in such benefits, advantages, or solutions, or cause such benefits, advantages, or solutions to become more pronounced are not to be construed as a critical, required, or essential feature or element of any or all the claims. As used herein and in the appended claims, the term "comprises," "comprising," or any other variation thereof is intended to refer to a non-exclusive inclusion, such that a process, method, article of manufacture, or apparatus that comprises a list of elements does not include only those elements in the list, but may include other elements not expressly listed or inherent to such process, method, article of manufacture, or apparatus.

What is claimed is:

1. A method of altering a biometric sensing and environmental sensing process in a portable communication device comprising:
   receiving a command over a wireless communication path;
   initiating a first sensor measurement of a sensed characteristic in response to said command;
   establishing an algorithm in said portable communication device in response to said command or said sensor measurement meeting a first criteria; and
   initiating a second sensor measurement using said algorithm.

2. The method of claim 1, further including the step of powering up the portable communication device in response to said command.

3. The method of claim 1, further including the step of determining a location of said portable communication device in response to said command.

4. The method of claim 3, further including the step of executing a power up algorithm in response to said location meeting a first criteria.

5. The method of claim 1, further including the step of sending a command in response to initiating a sensor measurement to a second portable communication device.

6. The method of claim 1, further including the step of initiating a sensor measurement in response to a predetermined program sequence prior to receiving said command.

7. The method of claim 6, requesting a command from a second device in response to said sensor measurement meeting a sensor measurement criteria.

8. The method of claim 1 prior to establishing said algorithm, determining if said algorithm is valid.

9. The method of claim 1 receiving said command from said wireless communication path over a RF communication path.

10. A method of context sensing for a portable communication device comprising:
    taking a first measurement with a first sensor coupled to said portable communication device; and
    initiating a second measurement with a second sensor not the same as said first sensor of said portable communication device in response to said first measurement.

11. The method of claim 10, taking an environmental measurement with an environmental sensor coupled to said portable communication device.

12. The method of claim 11, initiating a biosensing measurement in response to said taking said environmental measurement.

13. The method of claim 11, altering a biosensing algorithm in response to taking said environmental measurement.

14. The method of claim 10, taking a biosensing measurement with a biosensing sensor coupled to said portable communication device.

15. The method of claim 14, initiating an environmental measurement in response to said taking said biosensing measurement.

16. The method of claim 14, altering an environmental measurement algorithm in response to taking said biosensing measurement.

17. The method of claim 10, taking a location measurement of said portable communication device with a GPS coupled to said portable communication device.

18. The method of claim 17, initiating a biosensing measurement in response to said location measurement.

19. The method of claim 17, altering a biosensing algorithm in response to said location measurement.

20. The method of claim 17, initiating an environmental measurement in response to said location measurement.

21. The method of claim 17, altering an environmental algorithm in response to said location measurement.

22. A portable communication device for sensing biometrics and environmental characteristics, comprising:
- a transceiver to receive a command;
- a first sensor to sense a first contextual characteristic;
- a second sensor to sense a second contextual characteristic; and
- a controller coupled to said transceiver and said first sensor and said second sensor, said processor operable to dynamically determine a sensing sequence of said first and said second sensors by establishing an algorithm in response to the step of receiving a command or in response to the first measurement meeting a first criteria, and initiating a second sensor measurement using the algorithm.

23. The portable communication device of claim 22 wherein said command alters the operation of said portable communication device.

24. The portable communication device of claim 23 wherein said command is received from a wide area network communication link.

25. The portable communication device of claim 23 wherein said command is received from a second portable communication device over a wireless communication link.

26. The portable communication device of claim 23 wherein said controller is responsive to said command to initiate said second sensor to sense a sensed characteristic.

27. The portable communication device of claim 22, wherein said first sensor is an environmental sensor and wherein said second sensor is a biometric sensor.

28. The portable communication device of claim 27 wherein said environmental sensor is a temperature sensor.

29. The portable communication device of claim 27 wherein said environmental sensor is a location sensor.

30. The portable communication device of claim 27 wherein said environmental sensor is a photo sensor.

31. The portable communication device of claim 27 wherein said biometric sensor is a heart rate sensor.

32. The portable communication device of claim 27 wherein said biometric sensor is a blood pressure sensor.

* * * * *